(12) United States Patent
Svrluga et al.

(10) Patent No.: US 9,005,696 B2
(45) Date of Patent: Apr. 14, 2015

(54) MEDICAL DEVICE FOR BONE IMPLANT AND METHOD FOR PRODUCING SUCH A DEVICE

(71) Applicants: Richard C. Svrluga, Newton, MA (US); Laurence B. Tarrant, Cambridge, MA (US)

(72) Inventors: Richard C. Svrluga, Newton, MA (US); Laurence B. Tarrant, Cambridge, MA (US)

(73) Assignee: Exogenesis Corporation, Billerica, MA (US)

( * ) Notice: Subject to any disclaimer, the term of this patent is extended or adjusted under 35 U.S.C. 154(b) by 0 days.

(21) Appl. No.: 13/746,456

(22) Filed: Jan. 22, 2013

(65) Prior Publication Data
US 2013/0138212 A1 May 30, 2013

Related U.S. Application Data

(62) Division of application No. 12/537,353, filed on Aug. 7, 2009, now abandoned.

(60) Provisional application No. 61/086,986, filed on Aug. 7, 2008.

(51) Int. Cl.
*A61K 6/083* (2006.01)
*A61F 2/28* (2006.01)
*B05D 3/06* (2006.01)

(52) U.S. Cl.
CPC .. *A61F 2/28* (2013.01); *B05D 3/068* (2013.01)

(58) Field of Classification Search
USPC ........ 623/1.42; 424/423; 427/2.24, 2.25, 523, 427/524
See application file for complete search history.

(56) References Cited

U.S. PATENT DOCUMENTS

| 3,710,795 A | 1/1973 | Higuchi et al. |
| 4,542,752 A | 9/1985 | DeHaan et al. |
| 4,968,006 A | 11/1990 | Oliver |

(Continued)

FOREIGN PATENT DOCUMENTS

| EP | 2326356 A2 | 6/2011 |
| JP | 10-66721 A | 10/1998 |

(Continued)

OTHER PUBLICATIONS

Matsuo, J. et al. What size of cluster is most appropriate for SIMS? Applied Surface Science 255 (2008) pp. 1235-1238.

(Continued)

*Primary Examiner* — Dah-Wei D Yuan
*Assistant Examiner* — Andrew Bowman
(74) *Attorney, Agent, or Firm* — Burns & Levinson LLP; Jerry Cohen; David W. Gomes

(57) ABSTRACT

A bone implantable medical device made from a biocompatible material, preferably comprising titania or zirconia, has at least a portion of its surface modified to facilitate improved integration with bone. The implantable device may incorporate a surface infused with osteoinductive agent and/or may incorporate holes loaded with a therapeutic agent. The infused surface and/or the holes may be patterned to determine the distribution of and amount of osteoinductive agent and/or therapeutic agent incorporated. The rate of release or elution profile of the therapeutic agent may be controlled. Methods for producing such a bone implantable medical device are also disclosed and employ the use of ion beam irradiation, preferably gas cluster ion beam irradiation for improving bone integration.

6 Claims, 11 Drawing Sheets

(56) References Cited

U.S. PATENT DOCUMENTS

| | | | |
|---|---|---|---|
| 5,084,151 A | 1/1992 | Vallana et al. | |
| 5,123,924 A | 6/1992 | Sioshansi et al. | |
| 5,133,757 A | 7/1992 | Sioshansi et al. | |
| 5,163,958 A | 11/1992 | Pinchuk | |
| 5,419,760 A | 5/1995 | Narcisco | |
| 5,459,326 A | 10/1995 | Yamada | |
| 5,609,629 A | 3/1997 | Fearnot et al. | |
| 5,707,684 A | 1/1998 | Hayes et al. | |
| 5,763,504 A | 6/1998 | Matsuda et al. | |
| 5,814,194 A | 9/1998 | Deguchi et al. | |
| 5,817,326 A | 10/1998 | Nastasi | |
| 5,837,313 A | 11/1998 | Ding et al. | |
| 5,843,172 A | 12/1998 | Yan | |
| 6,120,847 A | 9/2000 | Yang et al. | |
| 6,143,354 A | 11/2000 | Koulik et al. | |
| 6,156,373 A | 12/2000 | Zhong et al. | |
| 6,207,282 B1 | 3/2001 | Deguchi et al. | |
| 6,331,227 B1 | 12/2001 | Dykstra et al. | |
| 6,451,871 B1 | 9/2002 | Winterton et al. | |
| 6,486,478 B1 | 11/2002 | Libby et al. | |
| 6,491,800 B2 | 12/2002 | Kirkpatrick et al. | |
| 6,635,082 B1 | 10/2003 | Hossainy et al. | |
| 6,641,607 B1 | 11/2003 | Hossainy et al. | |
| 6,656,162 B2 | 12/2003 | Santini, Jr. et al. | |
| 6,676,989 B2 | 1/2004 | Kirkpatrick et al. | |
| 6,716,444 B1 | 4/2004 | Castro et al. | |
| 6,746,773 B2 | 6/2004 | Llanos et al. | |
| 6,764,505 B1 | 7/2004 | Hossainy et al. | |
| 6,805,898 B1 | 10/2004 | Wu et al. | |
| 6,863,786 B2 | 3/2005 | Blinn et al. | |
| 6,984,404 B1 | 1/2006 | Talton et al. | |
| 7,041,130 B2 | 5/2006 | Santini, Jr. et al. | |
| 7,094,256 B1 | 8/2006 | Shah et al. | |
| 7,105,199 B2 * | 9/2006 | Blinn et al. | 427/2.24 |
| 7,163,555 B2 | 1/2007 | Dinh | |
| 7,431,959 B1 | 10/2008 | Dehnad | |
| 7,575,593 B2 | 8/2009 | Rea et al. | |
| 7,666,462 B2 | 2/2010 | Blinn et al. | |
| 7,758,636 B2 | 7/2010 | Shanley et al. | |
| 7,942,926 B2 | 5/2011 | Benco et al. | |
| 2002/0017454 A1 | 2/2002 | Kirkpatrick | |
| 2002/0139961 A1 | 10/2002 | Kinoshita et al. | |
| 2002/0188324 A1 | 12/2002 | Blinn et al. | |
| 2003/0009233 A1 | 1/2003 | Blinn et al. | |
| 2003/0143315 A1 | 7/2003 | Pui et al. | |
| 2004/0204750 A1 | 10/2004 | Dinh | |
| 2005/0025804 A1 | 2/2005 | Heller | |
| 2005/0043787 A1 | 2/2005 | Kutryk et al. | |
| 2005/0058684 A1 | 3/2005 | Shanley et al. | |
| 2005/0074602 A1 | 4/2005 | Bjursten et al. | |
| 2005/0079201 A1 | 4/2005 | Rathenow et al. | |
| 2005/0142163 A1 * | 6/2005 | Hunter et al. | 424/423 |
| 2005/0205802 A1 | 9/2005 | Swenson et al. | |
| 2005/0240100 A1 | 10/2005 | Wang et al. | |
| 2005/0244453 A1 | 11/2005 | Stucke et al. | |
| 2006/0093646 A1 | 5/2006 | Cima et al. | |
| 2006/0155370 A1 | 7/2006 | Brister | |
| 2006/0204546 A1 | 9/2006 | Nguyen et al. | |
| 2006/0210494 A1 | 9/2006 | Rabiei et al. | |
| 2007/0087034 A1 | 4/2007 | Blinn et al. | |
| 2007/0123974 A1 | 5/2007 | Park et al. | |
| 2007/0181820 A1 | 8/2007 | Hwang et al. | |
| 2008/0147177 A1 | 6/2008 | Scheuermann et al. | |
| 2008/0183281 A1 | 7/2008 | Rea et al. | |
| 2008/0243241 A1 * | 10/2008 | Zhao | 623/1.42 |
| 2008/0306579 A1 | 12/2008 | Dolan et al. | |
| 2009/0036373 A1 | 2/2009 | Lang | |
| 2009/0074834 A1 | 3/2009 | Kirkpatrick et al. | |
| 2009/0098186 A1 | 4/2009 | Kirkpatrick et al. | |
| 2010/0036502 A1 | 2/2010 | Svrluga et al. | |
| 2010/0098833 A1 | 4/2010 | Blinn et al. | |
| 2011/0086081 A1 | 4/2011 | To et al. | |

FOREIGN PATENT DOCUMENTS

| | | |
|---|---|---|
| WO | 02083039 A1 | 10/2002 |
| WO | 2004105826 A2 | 12/2004 |
| WO | 2007092894 A2 | 8/2007 |
| WO | 2008036357 A2 | 3/2008 |
| WO | 2009036373 A2 | 3/2009 |

OTHER PUBLICATIONS

Fehsenfeld P. et al., Production of Radioactive Stents:, Nachrichten Forschungszentrum Karlsruhe, 2000, pp. 81-86, vol. 32-1, Germany.

Translation of JP 10-66721, cited above (Oct. 3, 1998).

Free Online Dictionary, Carbonized (accessed Jan. 11, 2012), pp. 1-2.

International Search Report dated May 6, 2010 for International Application No. PCT/US09/53108.

International Search Report dated Nov. 5, 2012 for International Application No. PCT/US12/51816.

Extended European Search Report dated Oct. 31, 2013 for EP Application No. 09805598.1.

* cited by examiner

MEDICAL DEVICE FOR BONE IMPLANT AND METHOD FOR PRODUCING SUCH A DEVICE

CROSS REFERENCE TO RELATED APPLICATIONS

This application is a divisional of co-pending U.S. patent application Ser. No. 12/537,353, Filed Aug. 7, 2009, and entitled MEDICAL DEVICE FOR BONE IMPLANT AND METHOD FOR PRODUCING SUCH A DEVICE, which in turn claims priority from U.S. Provisional Patent Application S.N. 61/086,986, filed Aug. 7, 2006, both of which are incorporated herein by reference in their entirety for all purposes.

FIELD OF THE INVENTION

This invention relates generally to an implantable medical device for implantation into or onto a bone of a mammal and to a method for producing such an implantable medical device. More specifically, it relates to an implantable medical device made from a biocompatible material, preferably titanium (with a titania surface) or zirconia, with at least a portion of its surface parts modified to facilitate improved integration with bone. The invention also relates to a method for producing such an implant that includes the use of ion beam technology, preferably gas cluster ion beam technology.

BACKGROUND OF THE INVENTION

As used herein the term "titania" is intended to include oxides of titanium, and the titanium metal itself (or an alloy thereof) together with a surface coating of native oxide or other oxide comprising the element titanium (including without limitation $TiO_2$, and or $TiO_2$ with imperfect stoichiometry).

As used herein the term "zirconia" is intended to mean zirconium dioxide (even with imperfect stoichiometry) in any of its various forms (treated or untreated to toughen it for use in a bone implant) and any materials or ceramics that are at least 50% zirconium dioxide.

As used herein, the term "tricalcium phosphate" is intended to include without limitation beta tricalcium phosphate.

As used herein, the term "nutrient material" is intended to include any material that encourages osteoblasts to grow and produce bone components on a surface by providing a local nutrient source. Nutrient material examples include, without limitation, calcium phosphate-containing materials such as hydroxyapatite $[Ca_5(PO_4)_3(OH)]_x$(HA) or tricalcium phosphate $Ca_3(PO_4)_2$ (TCP); or other minerals or compounds having a composition similar to natural bone components including Bioglass 45S5 and Bioglass 58S; or compounds related to the foregoing but having imperfect stoichiometry; or other sources of Ca, $Ca^{++}$, P, O, $PO_4$, or $P_2O_5$; or molecular dissociation products including Ca, P, O, and H atoms, as well as larger fragments of the HA or TCP molecules.

As used herein, the term "BMP" is intended to include any of the bone morphogenic proteins that are useful in promoting the formation and/or attachment of new bone growth when applied in contact with or in proximity to a bone-implantable medical device.

As used herein, the term "bone growth-stimulating agent" is intended to include any material that stimulates and encourages the development and functional maintenance of mature osteoblasts. Bone growth-stimulating agents include, without limitation: growth factors; cytokines and the like, such as members of the Transforming Growth Factor-beta (TGF-β) protein superfamily including any of the Bone Morphogenic Proteins (BMP) and members of Glycosylphosphatidylinositol-anchored (GPI-anchored) signaling proteins including members of the Repulsive Guidance Molecule (RGM) protein family; and other growth regulatory proteins.

As used herein the term "osteoinductive agent" is intended to mean a nutrient material and/or a bone growth-stimulating agent.

As used herein, the term "hole" is intended to mean any hole, cavity, crater, trough, trench, or depression penetrating a surface of a bone-implantable medical device and may extend through a portion of the device (through-hole), or only part way through the device (blind-hole, or cavity) and may be substantially cylindrical, rectangular, or of any other shape.

As used herein, the term "bone-implantable medical device" is intended to include, without limitation, dental implants, bone screws, interference screws, buttons, artificial joint prostheses (as for example femoral bail prostheses or an acetabular cup prostheses) that attach to a bone, and endosseus implants, prostheses and supports or any implant that required the integration of bone with the implant, and ceramic, polymeric, metallic, or hybrid materials that are meant to affix ligaments, tendons, rotator cuffs, and the like soft skeletal tissues to bony tissues.

As used herein, the term "therapeutic. agent" is intended to mean a medicine, drug, antibiotic, anti-inflammatory agent, osteoinductive agent, BMP, or other material that is bioactive in a generally beneficial way.

Bone implantable medical devices intended for implant into or onto the bones of a mammal (including human) are employed as anchors for dental restoration, fasteners and/or prostheses for repair of bone fractures, joint replacements, and other applications requiring attachment to bone. It is known that titania and zirconia are among preferred materials for such bone-implantable medical devices because of the biocompatibility of the material and its ability to accept attachment of new bone growth, however other materials including stainless steel alloys, cobalt-chrome alloy, cobalt-chrome-molybdenum alloy, other ceramics in addition to zirconia, and other materials are also utilized. Bone-implantable medical devices are often fabricated from titanium metal (or alloy) that typically has a titania surface (either native oxide or otherwise). Bone-implantable medical devices may be coated (or partially coated) with (A) one or more nutrient materials or (B) one or more bone growth-stimulating agents. Such materials may be applied as a coating by a variety of techniques. Bone growth-stimulating agents may be introduced into a surgical implantation site or applied as coatings for implantable medical devices and also may serve to facilitate new bone growth and attachment for integration of the device into the bone. Bone growth-stimulating agents may be used as an alternative to or in combination with nutrient material coatings. Coatings of nutrient materials may be partial, and if totally contiguous on the surface, may actually discourage adhesion of the cells and bone integration by leaving exposed gaps on the surface as consumed.

Other problems exist, in that when such medical devices are being implanted into bone, the surfaces of the devices most intimately in contact with the preexisting bone often experience considerable mechanical abrasion and/or wiping by the bone. For example, an anchor for a dental implant often consists of a threaded screw portion that is screwed into a drilled bone hole and, which effectively becomes a self-tapping screw during implant, cutting its own threads in the drilled hole. Similarly, orthopedic bone screws for repairing fractures or attaching prostheses to immobilize fractures, also experience considerable abrading forces on the threaded surfaces during their surgical placement. An artificial hip joint prosthesis has a stem for insertion into a hole in a femur, and may be forcibly hammered into the opening during surgical implantation, undergoing abrading forces on the inserted stem. In such procedures, the aggressive abrasion of the surfaces of the medical devices during their implantation tends to abrade away or otherwise result in premature removal or release of attached osteoinductive agents. This results in reduced benefit from the osteoinductive coatings, which in turn results in longer times for complete integration of the implant into the bone. Longer integration times often correspond to delayed healing and increased costs and greater suffering for the mammal receiving the implant.

Bone-implantable medical devices having holes or grooves for retaining and delivering osteoinductive agents are known. This approach provides relief for some of the problems described above. However, in general, medicines so delivered may not be adequately retained and may migrate or elute out of the holes more rapidly than is desired for optimal effect. One response to this problem has been to mix the medicine with a polymer prior to loading it into the holes. This can result in slowed release of the medicine as the polymer biodegrades and/or erodes. Another response has been to load the medicine and then cover it with a polymer layer. This can result in delayed or slowed release. In either case the intent and effect is to delay and/or control the elution of the medicine from the hole, extending its therapeutic lifetime and effectiveness. There remain a number of problems associated with this polymer technology. Because of the mechanical forces involved in the implantation of a bone-implantable medical device, the polymeric material has a tendency to crack and sometimes delaminate. This modifies the medicine release rate from that which is intended and additionally the polymeric flakes can migrate through the osteosurgical site and cause unintended side effects. There is evidence to suggest that the polymers themselves cause a toxic reaction that may interfere with proper healing and with long-term success. Additionally, because of the volume of polymer required to adequately contain the medicine, the total amount of medicine that can be loaded may be undesirably reduced.

Gas cluster ion beams (GCIB) are generated and transported for purposes of irradiating a workpiece according to known techniques as taught for example in the published U.S. Patent Application 2009/0074834A1 by Kirkpatrick et al., the entire contents of which are incorporated herein by reference.

GCIB have been employed to smooth or otherwise modify the surfaces of implantable medical devices such as stents, joint prostheses and other implantable medical devices. For example, U.S. Pat. No. 6,676,989C1 issued to Kirkpatrick et al. teaches a GCIB processing system having a holder and manipulator suited for processing tubular or cylindrical workpieces. In another example, U.S. Pat. No. 6,491,800B2 issued to Kirkpatrick et al. teaches a GCIB processing system having workpiece holders and manipulators for processing other types of non-planar medical devices, including for example, hip joint prostheses. In view of the increasing use of surgical implants into or onto bone, the value of the use of osteoinductive agents, and the problems associated with state of the art practice, it is desirable to have bone-implantable medical devices that can be loaded with osteoinductive agents and which are resistant to the forces and abrasions encountered during the implantation process, thus providing superior retention for greater post-implant effectiveness.

It is therefore an object of this invention to provide bone-implantable medical devices having surfaces with improved retention of osteoinductive agents.

It is further an objective of this invention to provide methods of attaching and/or retaining osteoinductive agents on surfaces of bone-implantable medical devices.

Yet another objective of this invention is to provide bone-implantable medical devices and methods for their production that retain medicines or other therapeutic agents in holes with controlled release or elution rates and without the undesirable effects associated with the use of polymers by employing gas cluster ion beam technology.

SUMMARY OF THE INVENTION

The objects set forth above as well as further and other objects and advantages of the present invention are achieved by the invention described herein below.

The present invention is directed to the use of gas cluster ion beam processing to form one or more surface regions on bone-implantable medical devices, the surface regions having shallow layers including materials that are promoters of bone growth and adhesion. It is also directed to the use of holes in the medical device for containing a therapeutic agent such as for example a BMP. The shallow surface layers and the holes are resistant to abrasion and damage during implant into a bone.

Beams of energetic conventional ions, electrically charged atoms or molecules accelerated through high voltages, are widely utilized to dope semiconductor device junctions, to smooth or roughen surfaces by sputtering, and to enhance the properties of thin films. Unlike conventional ions, gas cluster ions are formed from clusters of large numbers (having a typical distribution of several hundreds to several thousands with a mean value of a few thousand) of weakly bound atoms or molecules of materials that are gaseous under conditions of standard temperature and pressure (commonly oxygen, nitrogen, or noble gases such as argon or xenon, for example, but any condensable gas can be used to generate gas cluster ions) sharing common electrical charges and which are accelerated together through high voltages (on the order of from about 3 kV to 70 kV or more) to have high total energies. Being loosely bound, gas cluster ions disintegrate upon impact with a surface and the total energy of the accelerated gas cluster ion is shared among the constituent atoms. Because of this energy sharing, the atoms are individually much less energetic than as is the case for conventional ions or ions not clustered together and, as a result, the atoms penetrate to much shorter depths, despite the high energy of the accelerated gas cluster ion.

Because the energies of individual atoms within a gas cluster ion are very small, typically a few eV to some tens of eV, the atoms penetrate through, at most, only a few atomic layers of a target surface during impact. This shallow penetration (typically a few nanometers or less to about ten nanometers, depending on the beam acceleration) of the impacting atoms means all of the energy carried by the entire cluster ion is consequently dissipated in an extremely small volume in a very shallow surface layer during a time period less than a microsecond. This is different from using conventional ion beams where the penetration into the material may be much greater, sometimes several hundred nanometers, producing changes and material modification deep below the surface of the material (depending on ion beam energy). Because of the high total energy of the gas cluster ion and extremely small interaction volume due to shallow penetration, the deposited energy density at the impact site is far greater than in the case of bombardment by conventional ions. Accordingly, at the point of impact of a gas cluster ion on a substrate such as a metal, oxide, or ceramic, there is a momentary (less than a microsecond) high temperature and high pressure transient condition that results in dissociation of the gas cluster and can result in dissociation of molecules, as for example HA or other osteoinductive agent or agents, that may be on the surface of the metal, oxide, or ceramic. The transient extreme conditions can drive the molecular dissociation products and perhaps entire molecules from their positions on the surface into the surface of the metal, oxide, or ceramic substrate in a process referred to as "infusion" or "infusing". The molecules of osteoinductive agent and/or dissociation products of the molecules of osteoinductive agent thereby become embedded in and incorporated into the surface and shallow subsurface of the substrate. The more volatile and less chemically reactive dissociation products and the volatile and unreactive components of the gas cluster ions may tend to escape to a greater degree, while the less volatile and/or more reactive dissociation products tend to become infused (and therefore embedded or partially embedded) into a very shallow surface layer (about 1 to about 10 nanometers thick) of the substrate, with many of the dissociation products exposed at the surface where they are available for chemical reaction with both the substrate surface and with surrounding materials from the surgical site and thus are positioned to be able to promote new bone growth and attachment to the substrate. Such a surface layer is referred to as an "infused surface layer" or a "GCIB infused surface layer". For HA (as an example), dissociation products may include Ca, P, O, and H atoms, as well as larger fragments of the HA molecule. The infused surface may also have its crystallinity modified from that of the original pre-infusion substrate surface by the action of the GCIB cluster impacts, typically resulting in conversion to a more amorphous or less crystalline structure.

For this reason, the GCIB is capable of transforming a titania or zirconia surface which has a thin coating of osteoinductive agent into a surface that is primarily titania or zirconia, but having a very thin infused layer containing for example, Ca, P, O, and H atoms (and/or ions) as well as larger fragments osteoinductive agent molecules, and possibly also embedded and/or partially embedded osteoinductive agent molecules. These infusion products are intimately embedded (wholly and/or partially) in the metal, oxide, or ceramic substrate subsurface to a depth of up to about 10 nanometers and many are exposed at the surface and available for promotion of and attachment to new bone growth. Such a surface is said to be infused with osteoinductive agent. An osteoinductive agent-infused titania or zirconia surface inherits beneficial characteristics of the osteoinductive agents that are infused into the surface, especially so in the ease of nutrient materials. A unique characteristic of an osteoinductive agent-infused surface of a surgical implant of for example titania or zirconia is that in addition to the availability of the infusion products at the surface, considerable amounts of the original substrate material (for example titania or zirconia) are also exposed at the surface of the infused region, thus the implant site sees both the availability of the osteoinductive agent and its fragments as well as the biocompatibility features of the titania or zirconia. By controlling the portion of the implant that is coated, more or less of the surface can be processed. In one embodiment, more of the original titania or zirconia is exposed at the surface than is the osteoinductive agent.

The metal, oxide, or ceramic surface can optionally also be provided with small holes that are loaded with a medicine such as BMP or an antibiotic, or other medicine that promotes the effectiveness of a bone implant.

Osteoinductive agent coatings may be applied to a bone-implantable medical device by any of several methods, including for examples, spraying a suspension of ultra-fine particles, spraying a solution, precipitation from solution, dipping, electrostatic deposition, ultrasonic spraying, plasma spraying, and sputter coating. When coating, a conventional masking scheme may be employed to limit deposition to selected locations. A coating thickness of from about 0.01 to about 5 micrometers may be utilized.

In one embodiment, the bone-implantable medical device or portions of the bone-implantable medical device) may be cleaned by GCIB irradiation prior to applying the osteoinductive agent coating.

After the titania or zirconia has been coated with an osteoinductive agent, it is processed by ion beam (preferably GCIB) irradiation to form an osteoinductive agent-infused surface.

Optionally, the titania or zirconia surface may have holes, and the holes may additionally be loaded with a therapeutic agent. Holes may be of selected size or sizes and pattern to control the dose of the medicine and the distribution of the medicine on the titania or zirconia surface.

BRIEF DESCRIPTION OF THE DRAWINGS

For a better understanding of the present invention, together with other and further objects thereof, reference is made to the accompanying drawings, wherein.

DETAILED DESCRIPTION OF THE DRAWINGS

Figure 1:
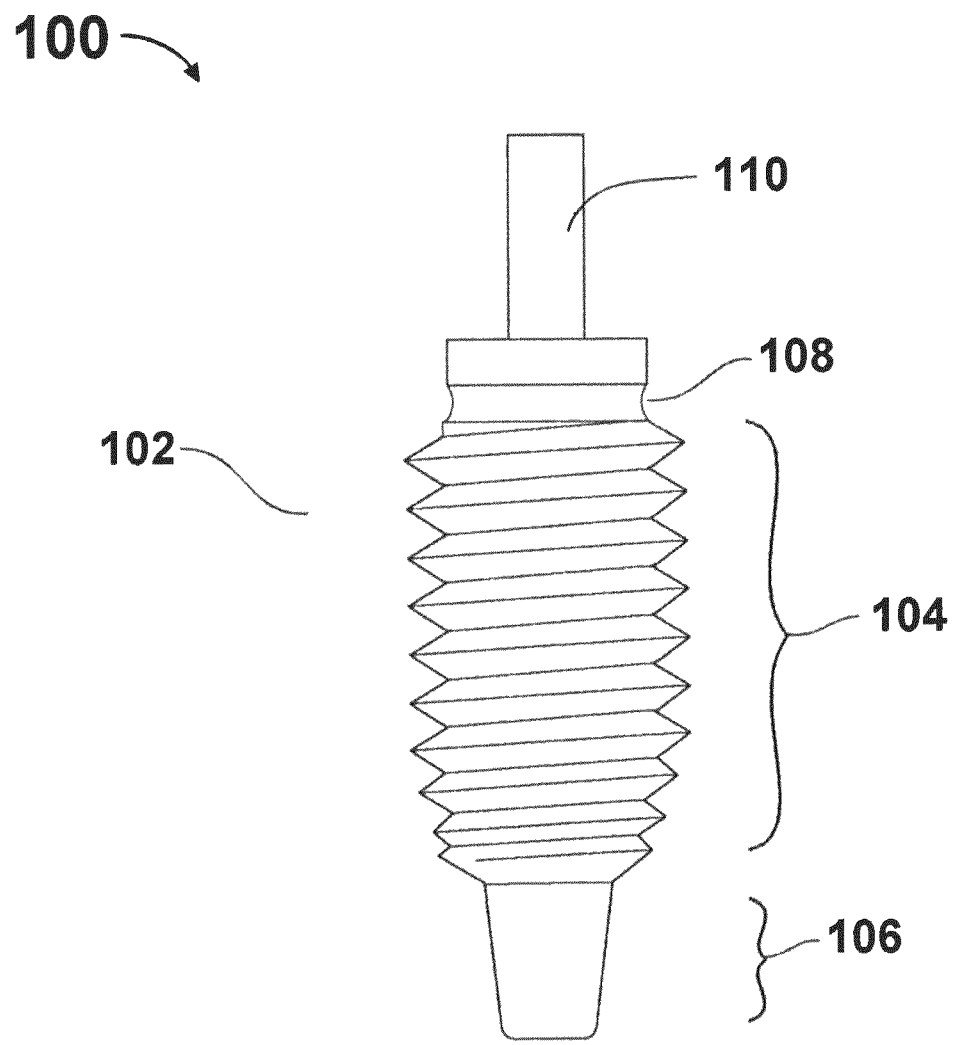
FIG. 1 is a view of a prior art bone-implantable medical device, a dental implant device.

Reference is now made to FIG. 1, which shows a view 100 of a prior art bone-implantable medical device in the form of a prior art dental implant 102. The prior art dental implant 102 is used for insertion into and implantation into a hole in a jawbone to form a basis for attaching a dental prosthesis, such as a prosthetic tooth or a dental restoration, for example. Drilling or other surgical techniques are typically employed to form the jawbone hole. The prior art dental implant 102 has a post 110 for attachment of a dental prosthesis (not shown). It has an implantable portion consisting of a threaded portion 104 and an unthreaded portion 106. A neck 108 connects the implantable portion with the post 110. The prior art dental implant 102 may be a single piece, or a composite of two or more pieces joined by any of a variety of known fastening techniques. In general the materials of the outer surfaces of the implantable portion are formed from biocompatible materials, often metal, oxide, or ceramic, preferably titanium with a titania (native or otherwise) surface or zirconia. Prior art dental implants are manufactured according to numerous different configurations, but in general they all have an implantable portion intended to be implanted into a hole or otherwise attached to a bone. The prior art dental implant 102 has a threaded portion 104 intended to intimately engage a hole in a bone, where if the implant is successful, it eventually becomes integrated with the bone by regrowth of new bone material.

Figure 2A:
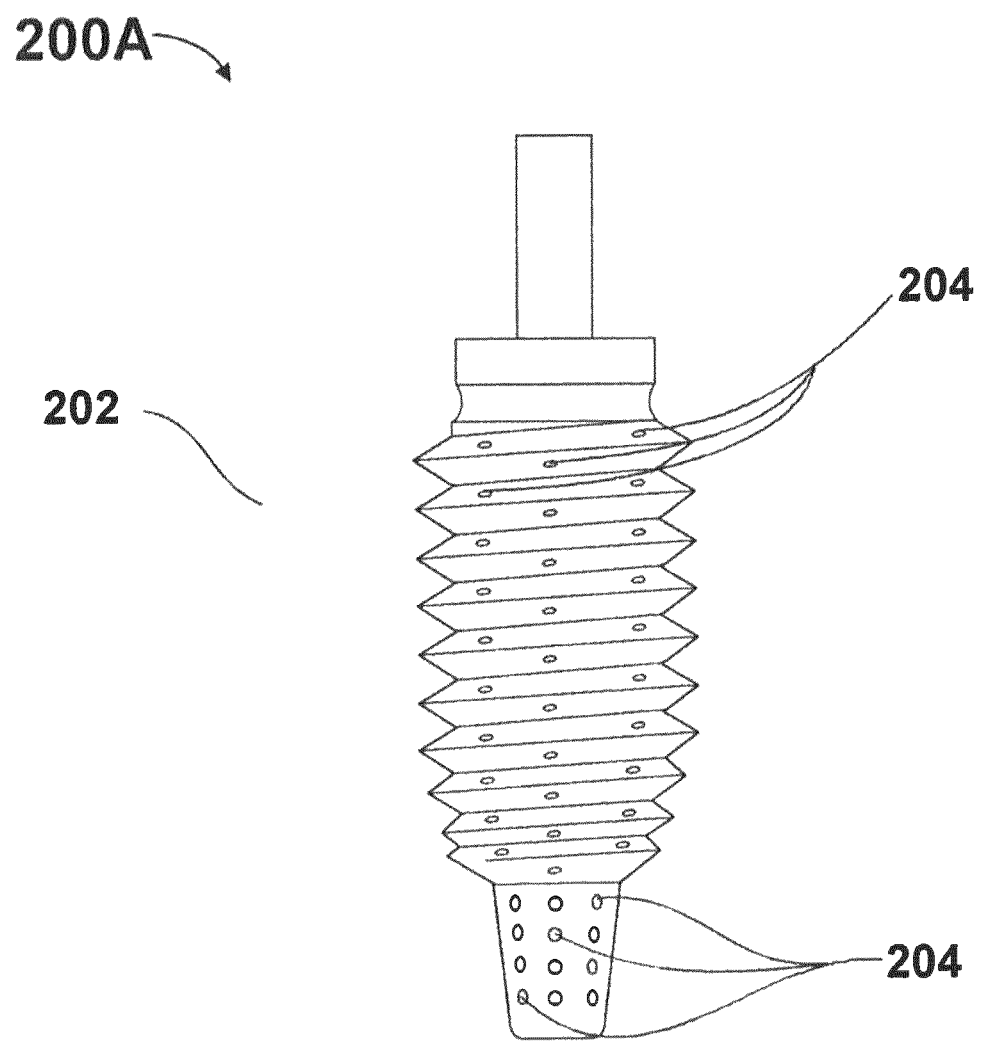
FIG. 2A is a view of a dental implant device with holes for loading an osteoinductive agent or other medicine as may be employed in embodiments of the invention.

FIG. 2A is a view 200A of a bone-implantable medical device in the form of a dental implant 202 as may be employed in an embodiment of the present invention. Dental implant 202 is an improved form of the prior art dental implant 102 (as shown in FIG. 1). Referring again to FIG. 2A, the implantable portion of the dental implant 202 preferably has a titania surface and has a multiplicity of holes (examples indicated by 204, not all holes labeled). Although shown in a particular pattern for explaining the invention, the particular pattern shown is not essential to the invention and it is understood that many and varied patterns can be employed in various embodiments of the invention. The relative sizes of the dental implant 202 and the holes 204 are not necessarily shown to scale. The holes may have a wide range of sizes and shapes. The holes 204 can be formed by a variety of techniques, but the methods of laser machining and focused ion beam machining are preferable because they can be controlled with great precision and can produce small, deep holes. The holes 204 may he, for example from about 50 micrometers to about 500 micrometers in diameter (or width) and may have an aspect ratio (diameter or width to depth) of about 0.5 to about 10 or even more. The holes 204 may be circular as indicated in FIG. 2 or in the form of grooves, trenches, other shapes, or combinations. The holes 204 may be of a variety of different diameters (or widths) and aspect ratios and (if grooves or trenches) lengths and shapes, so as to have differing volumes. The holes 204, empty at this process step, are provided for holding one or more therapeutic agents as for example BMP and/or antibiotics, anti-inflammatory agents, etc.

Figure 2B:
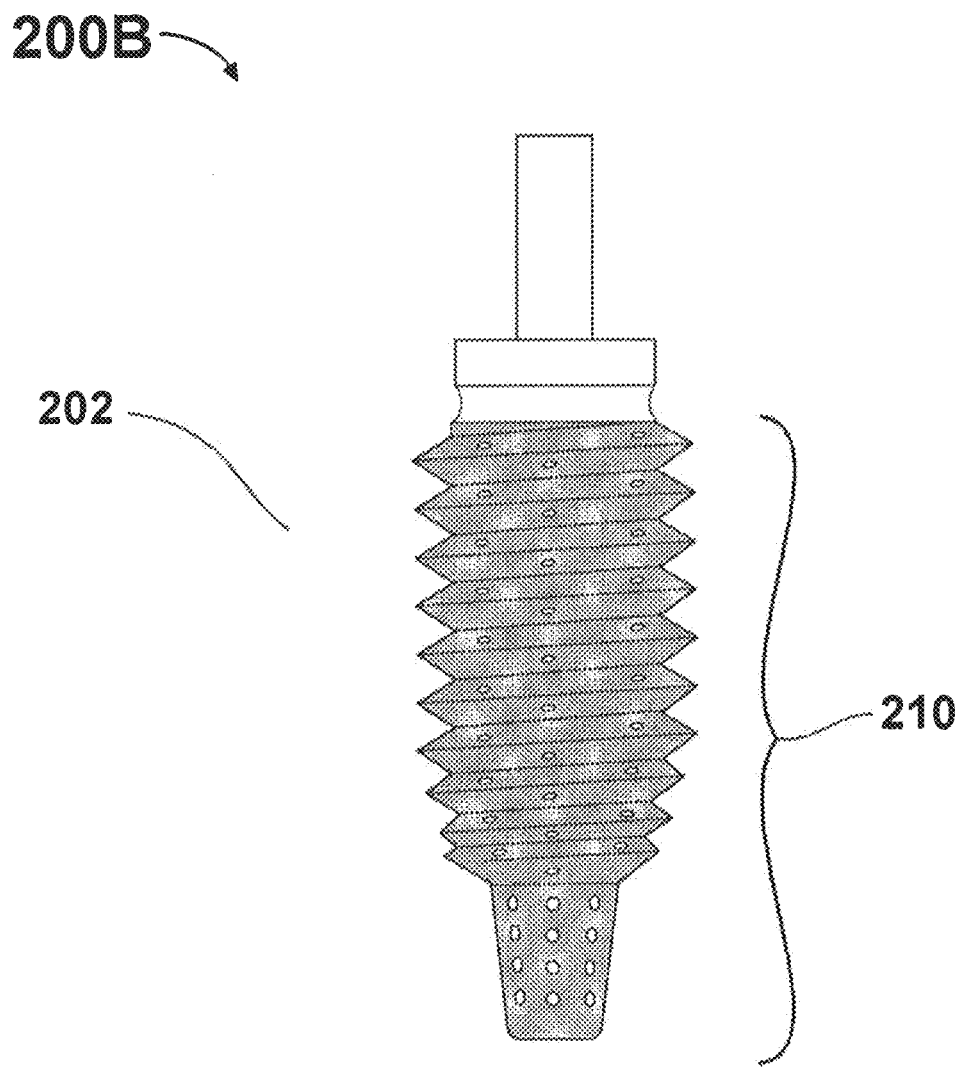
FIG. 2B is a view of a dental implant device with selected portions of its surface coated with an osteoinductive agent according to an embodiment of the invention.

FIG. 2B is a view 200B of the dental implant 202, after additional processing according to an embodiment of the invention. A portion of the surface of the dental implant is shown as coated with an osteoinductive agent, for example HA. The coated surface portion 210 (indicated in the figure by coarse stippling), in this case corresponds with the surface of the implantable portion of the dental implant 202, but could alternatively be one or more smaller regions of the implantable portion of the dental implant 202, with other regions uncoated. The osteoinductive agent coating may be applied by any of several methods, including for examples spraying or suspension of ultra-fine particles, precipitation from solution, dipping, electrostatic deposition, ultrasonic spraying, plasma spraying, and sputter coating. During coating, a conventional masking scheme may be employed to limit deposition to a selected location or locations. A coating thickness of from about 0.01 to about 5 micrometers may preferably be utilized. At this step of the process, the coating of osteoinductive agent is still susceptible to the problems described above—it can be abraded away or otherwise undesirably removed during the mechanical stresses of implantation into bone.

Figure 2C:
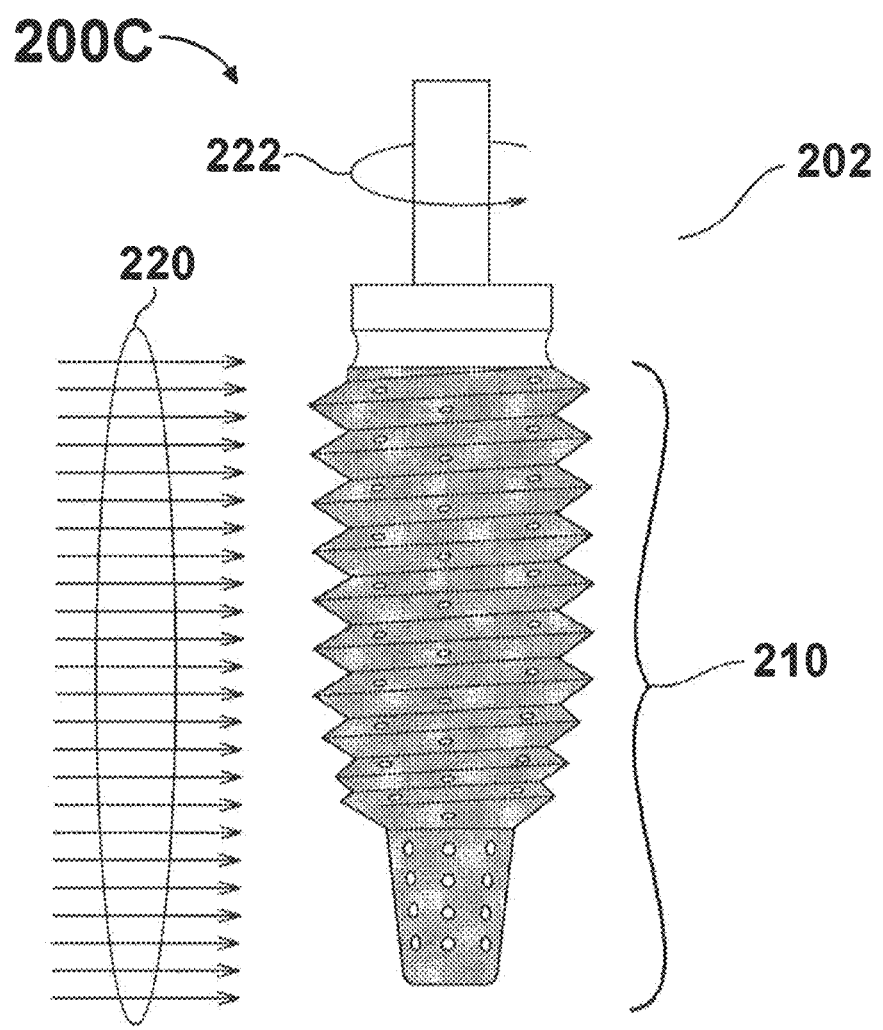
FIG. 2C shows an ion beam irradiation step in the formation of a GCIB infused layer in portions of the surface of a dental implant device according to an embodiment of the invention.

FIG. 2C shows a view 200C of the dental implant 202 after a portion of the surface has been coated with osteoinductive agent. An ion beam, preferably GCIB 220 is now employed to irradiate the coated surface portion 210 of the dental implant 202 to form a thin osteoinductive agent-infused layer in the preferably titanic or zirconia surface of the implantable portion of the dental implant 202 wherever the coated surface portion 210 previously existed. However, if for any reason it is not desired to form an osteoinductive agent-infused layer at any portion of the osteoinductive agent-coated surface, a conventional masking scheme or controlled direction of the GCIB 220 may be employed to limit irradiation to selected locations. Although the infused layer has been described, for example, as an HA-infused layer it will be readily understood, that if a different osteoinductive agent is used to form the coated surface portion 210, then the infused layer will be an infused layer of the different agent. In infusing the osteoinductive agent into the surface of the dental implant 202, a GCIB 220 comprising preferably argon cluster ions or oxygen cluster ions may be employed. The GCIB 220 may be accelerated with an accelerating potential of from 5 kV to 70 kV or more. The coating may be exposed to a GCIB dose of at least about $1\times10^{14}$ gas cluster ions per square centimeter. The GCIB irradiation step produces an osteoinductive agent-infused layer within the immediate surface of the titania or zirconia that is on the order of from about 1 to about 10 nanometers thick. While performing the ion beam irradiation, it is preferable to rotate the dental implant 202 about its axis with a rotary motion 222 during irradiation to assure that the desired ion dose is achieved on the entire coated surface portion 210. U.S. Pat. No. 6,676,989C1 issued to Kirkpatrick et al. teaches a GCIB processing system having a holder and manipulator suited for rotary processing tubular or cylindrical workpieces such as vascular stents and with routine adaptation, that system is also capable of the rotary irradiation required for this invention. In certain cases it may be desirable to infuse larger quantities of osteoinductive agent than can conveniently be done in a single coating and GCIB irradiation. In such cases, it is within the scope of the invention to repeat (one or more times) the steps of (a) coating the desired areas of the dental implant 202 with osteoinductive agent, and (b) irradiating the coated areas with GCIB to infuse the additional osteoinductive agent (using the techniques described herein in the descriptions of FIGS. 2B and 2C.

Figure 2D:
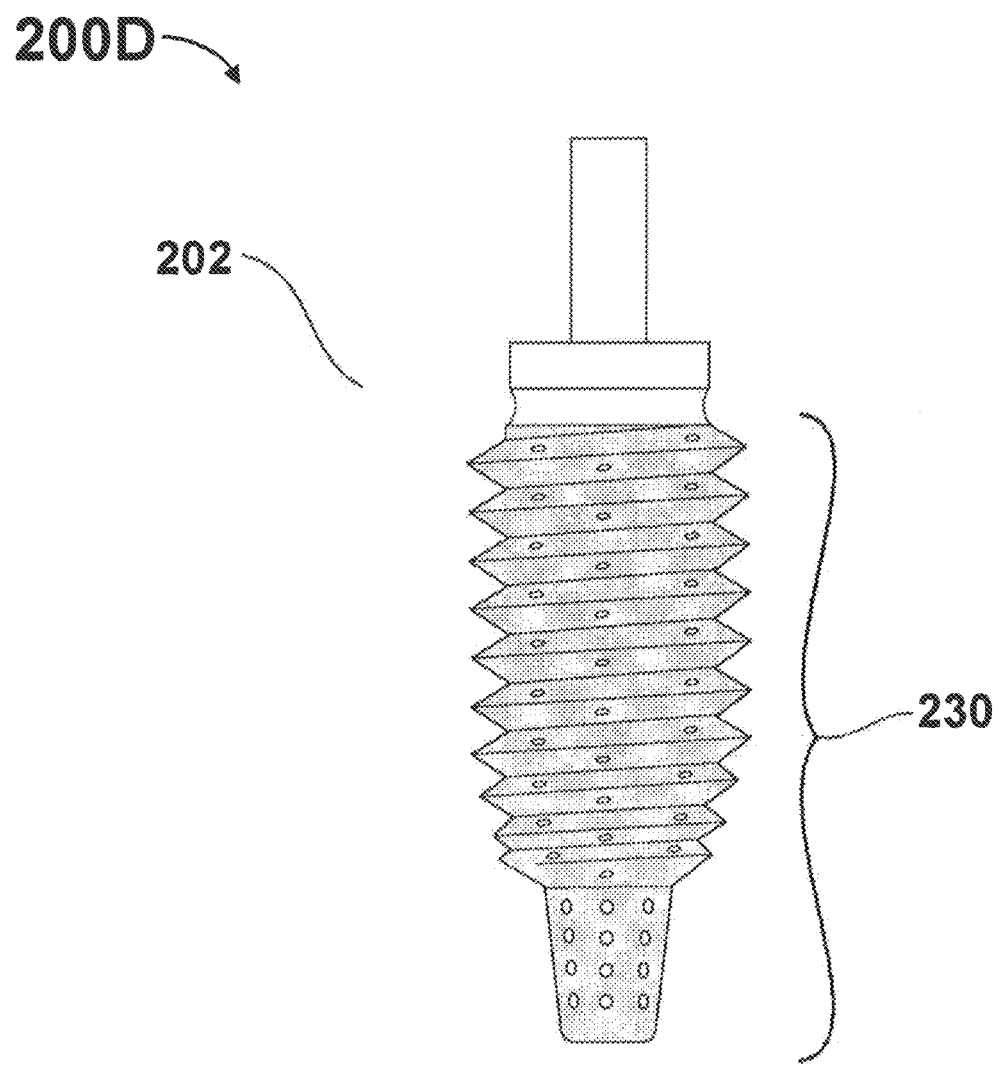
FIG. 2D shows a view of a dental implant device having a surface with an infused osteoinductive agent according to an embodiment of the invention.

FIG. 2D shows a view 200D of the dental implant 202 following the HA infusion step. The osteoinductive agent-coated portion has been fully converted to an osteoinductive agent-infused surface region 230 according to an embodiment of the invention.

Figure 2E:
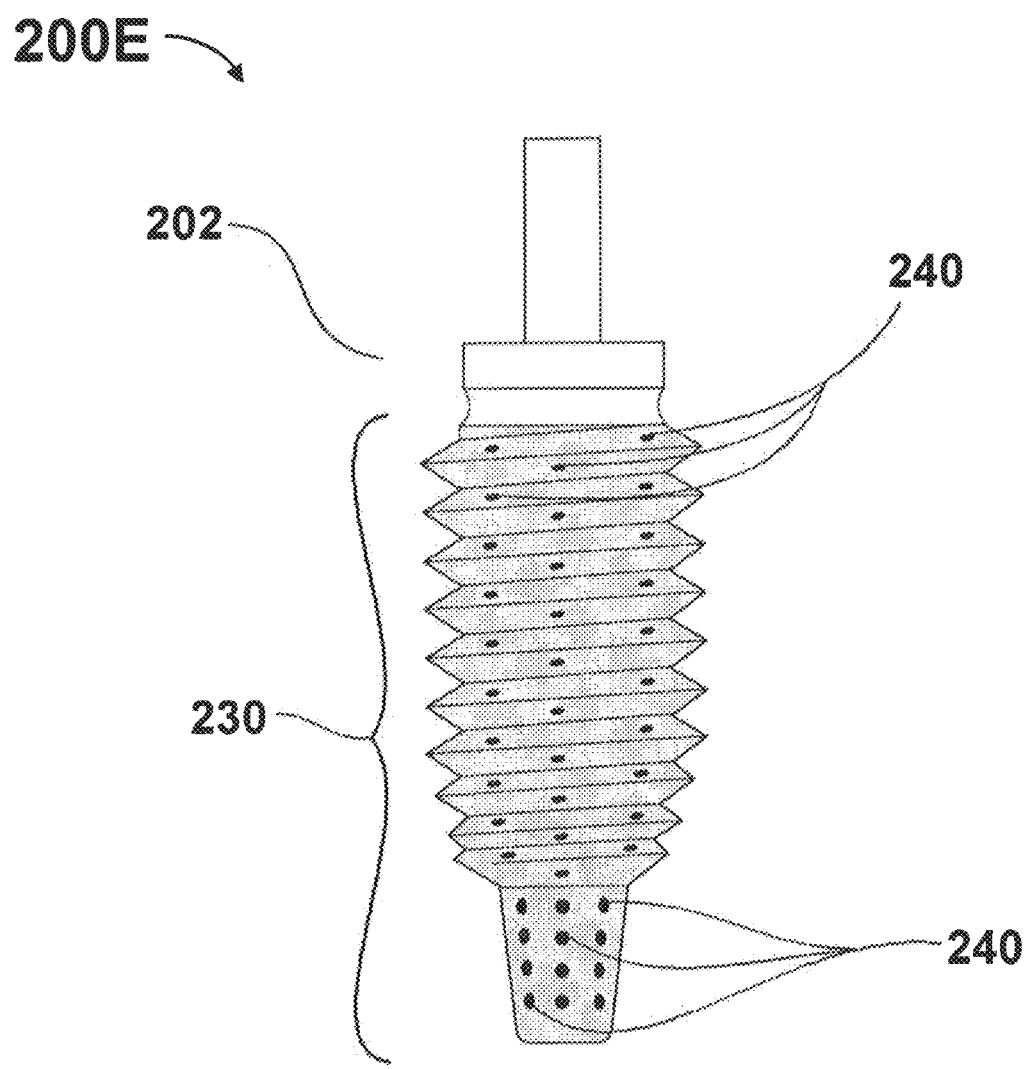
FIG. 2E shows a view of a dental implant device with an infused osteoinductive agent on a portion thereof, further having holes that are loaded with a medicine and/or an osteoinductive agent according to an embodiment of the invention.

FIG. 2E shows a view 200E of a dental implant 202, having an osteoinductive agent infused surface region. At this step, the holes 204 (as shown in FIG. 2A) are now loaded with a therapeutic material, forming loaded holes 240 (again referring to FIG. 2E). The loading of the therapeutic material may be done by any of numerous methods, including spraying, dipping, wiping, electrostatic deposition, ultrasonic spraying, vapor deposition, or by discrete droplet-on-demand fluid jetting technology. When spraying, dipping, wiping, electrostatic deposition, ultrasonic spraying, vapor deposition, or similar techniques are employed, a conventional masking scheme may be beneficially employed to limit deposition to a hole or to several or all of the holes in the dental implant 202. For liquids and solutions, discrete droplet-on-demand fluid-jetting is a preferred deposition method because it provides the ability to introduce precise volumes of liquid materials or solutions into precisely programmable locations. Discrete droplet-on-demand fluid jetting may be accomplished using commercially available fluid-jet print head jetting devices as are available (for example, not limitation) from MicroFab Technologies, Inc., of Plano, Tex. When the therapeutic material is a liquid, liquid suspension, or a solution, it is preferably dried or otherwise hardened before proceeding to the next step. The drying or hardening step may include baking, low temperature baking, or vacuum evaporation, as examples.

Figure 2F:
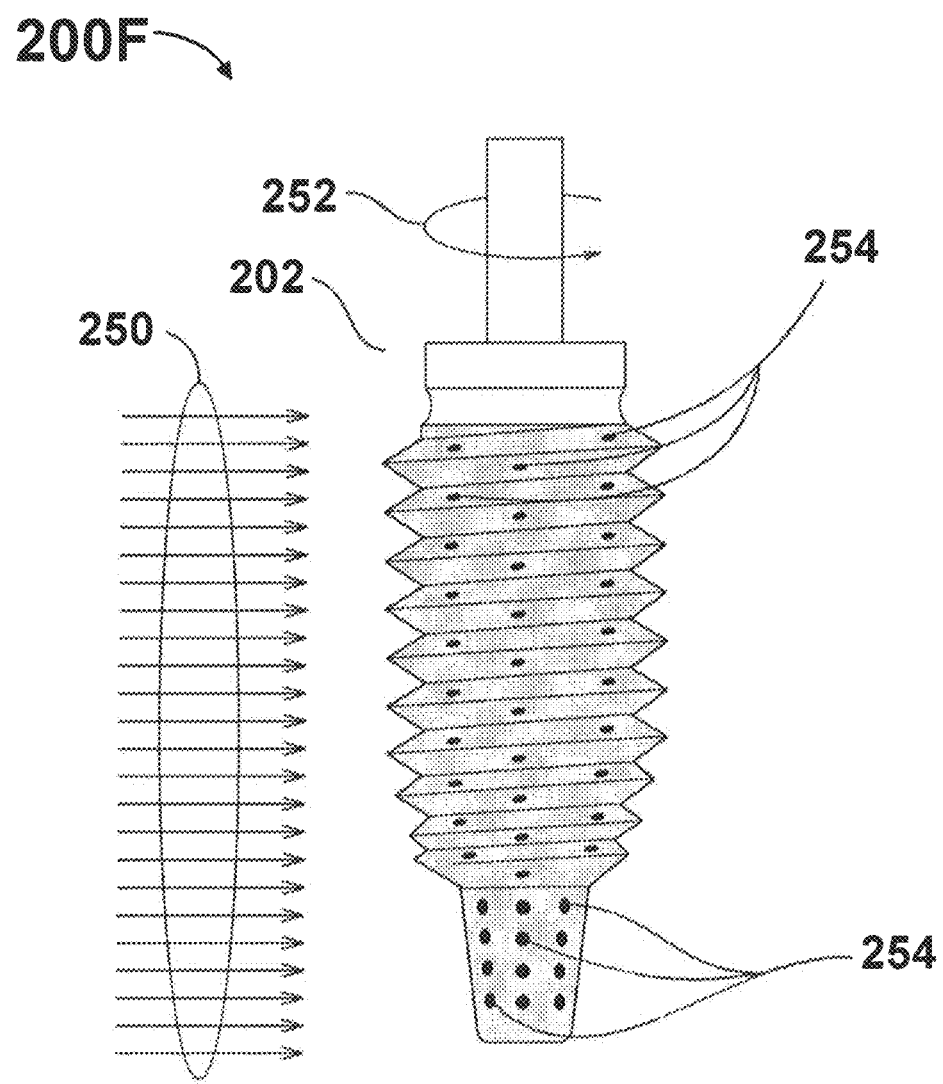
FIG. 2F shows a GCIB irradiation step in the formation of a thin barrier layer in the surface of therapeutic agent loaded in holes in a dental implant device according to an embodiment of the invention.

FIG. 2F is a view 200F showing an ion irradiation step in the formation of a thin barrier layer in the surface of the therapeutic agent loaded in the holes in the dental implant 202. An ion beam, preferably GCIB 250 is now employed to irradiate the surface of the therapeutic agent in the loaded holes 240 (see FIG. 2E) in the dental implant 202 to form a thin barrier layer at the surface to the therapeutic agent, forming loaded holes with thin barrier layers 254 at the exposed surface. The GCIB 250 forms a thin barrier layer at the surface of the therapeutic agent in the holes by modification of a thin upper region of the therapeutic agent. The thin barrier layer consists of therapeutic agent modified so as to density, carbonize or partially carbonize, denature, cross-link, or polymerize molecules of the therapeutic material in the thin uppermost layer of the therapeutic material. The thin barrier layer may have a thickness on the order of about 10 nanometers or even less. Additional details on the thin barrier layer and the process of its formation are described hereinafter in the discussion of FIGS. 3C and 3D.

FIGS. 3A, 3B, 3C, and 3D show detail of the steps for loading holes in a bone-implantable medical device with a therapeutic agent, and forming a thin barrier layer thereon far controlling retention and elution of the therapeutic agent by using GCIB irradiation.

Figure 3A:
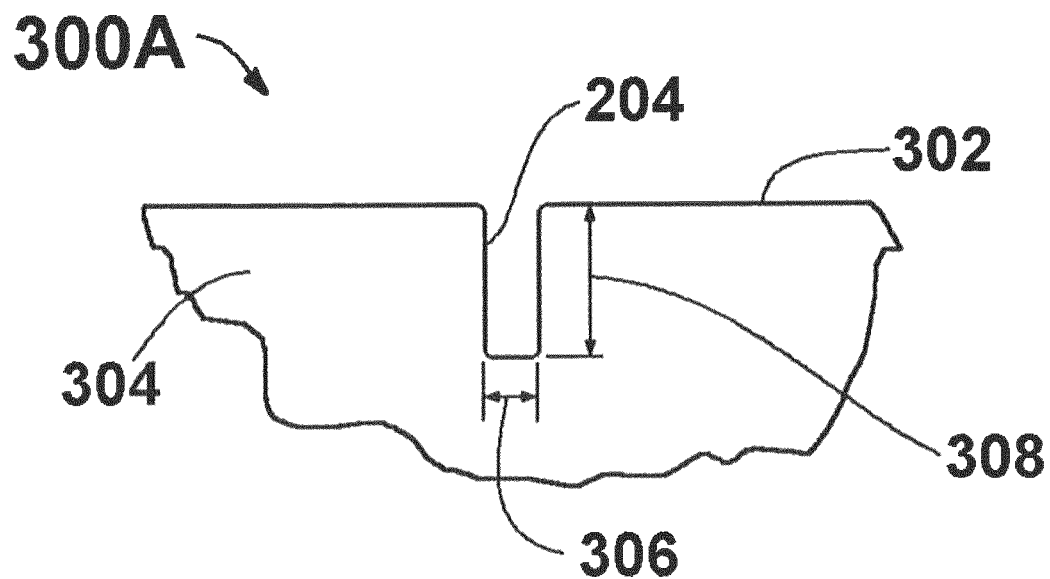
FIGS. 3A, 3B, 3C, and 3D show detail of the steps for loading a hole in a bone-implantable medical device with a therapeutic agent, and forming a thin barrier layer thereon using ion beam irradiation according to embodiments of the invention.

FIG. 3A shows a view 300A of a portion 304 of a surface 302 of a dental implant 202 (as shown in at the stage indicated in FIG. 2D, i.e., having an osteoinductive agent-infused surface region according to the invention), wherein the surface 302 represents a portion of the osteoinductive agent-infused surface region. Again referring to FIG. 3A, the portion 304 of the surface 302 of the dental implant 202 has a hole 204 having a diameter 306 and a depth 308. In this instance the hole 204 is intended to represent a substantially cylindrical hole, but as previously explained, other hole configurations are expected within the scope of the invention and the cylindrical nature of the hole is not intended to be limiting, but rather for clear explanation of the invention. The hole 204 is at a stage of readiness for loading with a therapeutic agent.

Figure 3B:
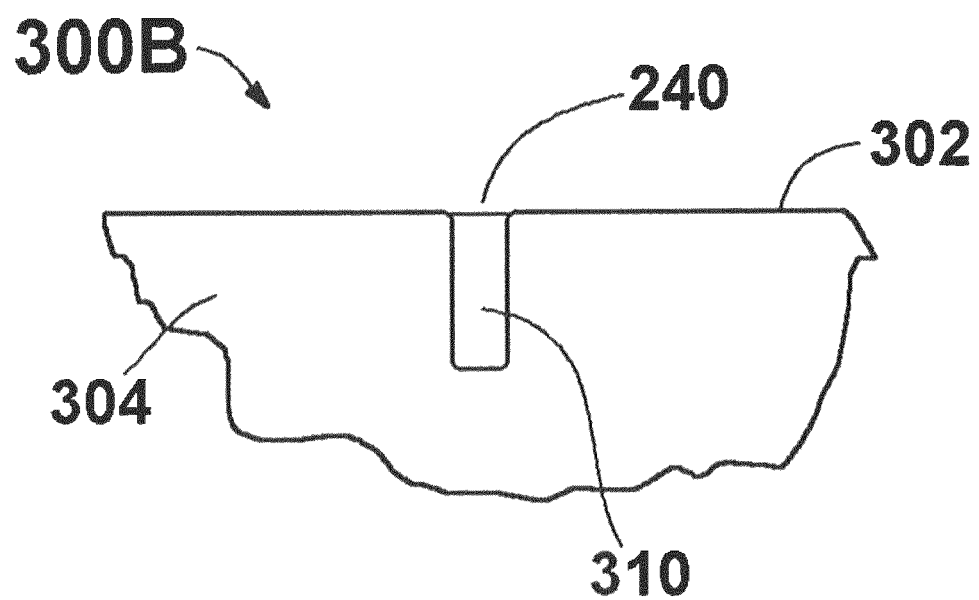

FIG. 3B shows a view 300B of a portion 304 of a surface 302 of a dental implant 202 with an osteoinductive agent-infused surface region. In this stage, the hole 204 has been loaded with a therapeutic agent 310, forming a loaded hole 240, corresponding to the loaded hole of FIG. 2E.

Figure 3C:
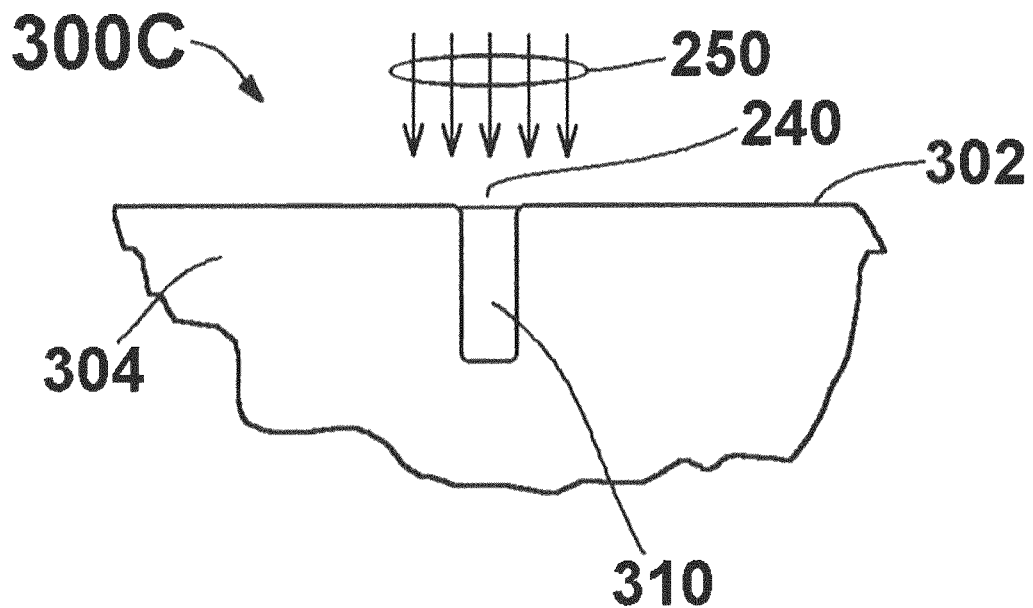

FIG. 3C shows a view 300C of a portion 304 of a surface 302 of a dental implant 202 with an osteoinductive agent-infused surface region and a loaded hole 240 loaded with therapeutic agent 310. An ion beam, preferably GCIB 250 is directed at the surface of the therapeutic agent 310 for the purpose of modifying the uppermost part of the surface of the therapeutic agent 310 to form a barrier layer. The therapeutic agent 310 is irradiated by the GCIB 250 modify of a thin upper region of the surface of the therapeutic agent 310. In modifying the surface, a GCIB 250 comprising preferably argon cluster ions or cluster ions of another inert gas may be employed. The GCIB 250 is may be accelerated with an accelerating potential of from 5 kV to 50 kV or more. The upper surface of the therapeutic agent 310 is may be exposed to a GCIB dose of at least about $1 \times 10^{13}$ gas cluster ions per square centimeter.

Figure 3D:
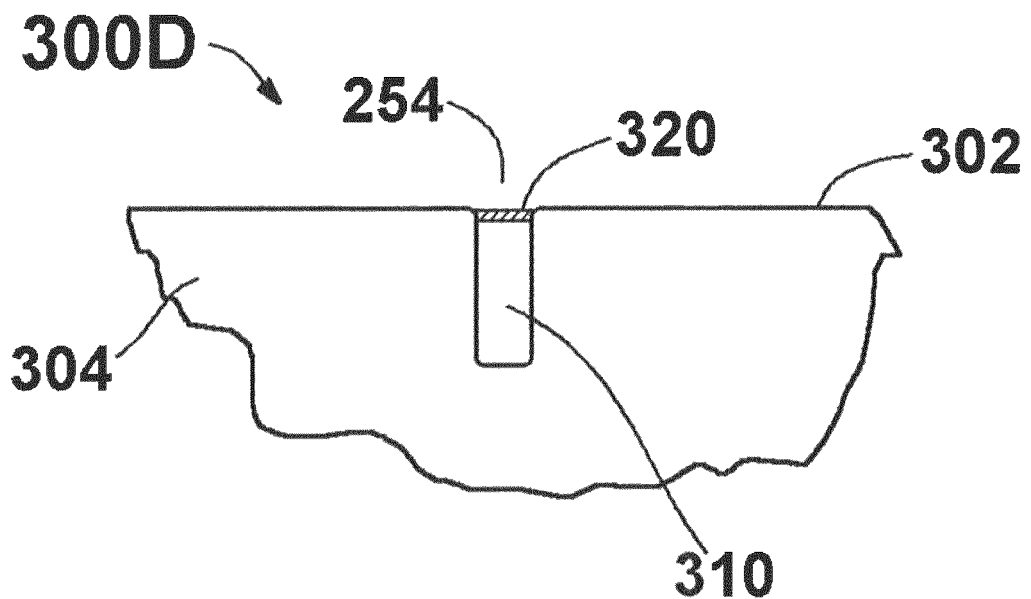

FIG. 3D shows a view 300D of a portion 304 of a surface 302 of a dental implant 202 with an osteoinductive agent-infused surface region and a hole 254 that is loaded with a therapeutic agent 310 upon which has been formed a thin barrier layer 320 by ion irradiation of the uppermost surface of the therapeutic agent 310. The thin barrier layer 320 consists of therapeutic agent 310 modified so as to densify, carbonize or partially carbonize, denature, cross-link, or polymerize molecules of the therapeutic agent in the thin uppermost layer of the therapeutic agent 310. The thin barrier layer 320 may have a thickness on the order of about 10 nanometers or even less. By selecting the dose and/or accelerating potential of the GCIB 250 (FIGS. 2F and 3C), the characteristics of the thin barrier layer 320 may be adjusted to permit control of the elution rate and/or the rate of inward diffusion of water and/or other biological fluids when the dental implant 202 is implanted in bone. In general, increasing acceleration potential increases the thickness of the thin barrier layer that is formed, and modifying the GCIB dose changes the nature of the thin barrier layer by changing the degree of cross linking, densification, carbonization, denaturization, and/or polymerization that results. This provides means to control the rate at which the therapeutic agent 310 will subsequently release or elute through the barrier and/or the rate at which water and/or biological fluids my diffuse into the drug from outside the dental implant 202.

Figure 4:
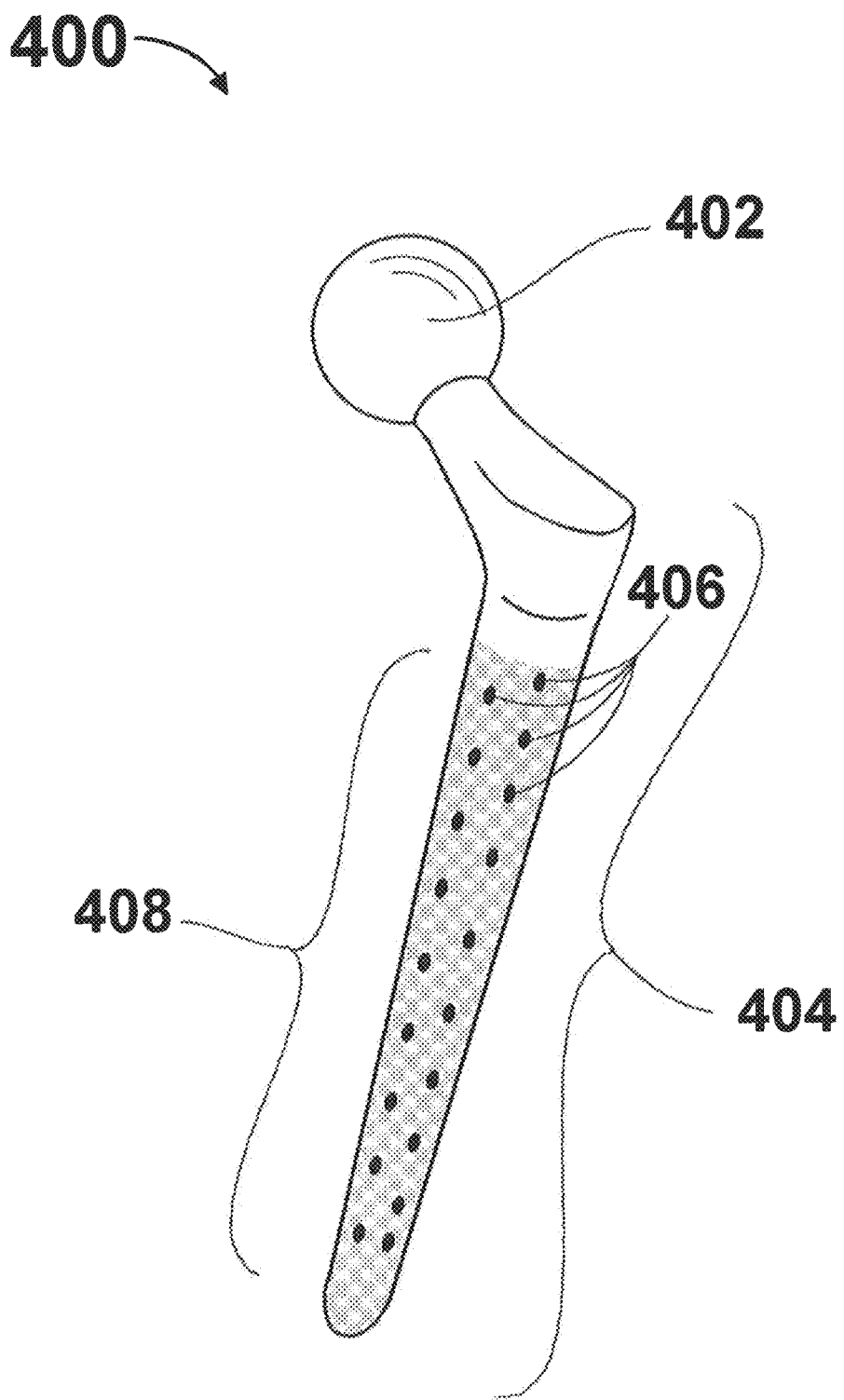
FIG. 4 shows a bone-implantable hip joint prosthesis employing embodiments of the invention.

FIG. 4 shows a bone-implantable medical device in the form of an artificial hip joint prosthesis 400 for replacement of a femoral ball. The prosthesis 400 has a ball 402 for replacement of the ball portion of the natural joint and has a stem 404 for insertion into and for integration with the femur. According to the invention, a portion 408 of the surface of the stem 404 has been osteoinductive agent-infused by osteoinductive agent-coating followed by ion irradiation (preferably GCIB irradiation) and has a pattern of holes 406 that are loaded with a therapeutic agent and which have been ion irradiated (preferably GCIB irradiated) to form thin barrier layers for control of elution rate of the therapeutic agent.

Figure 5:
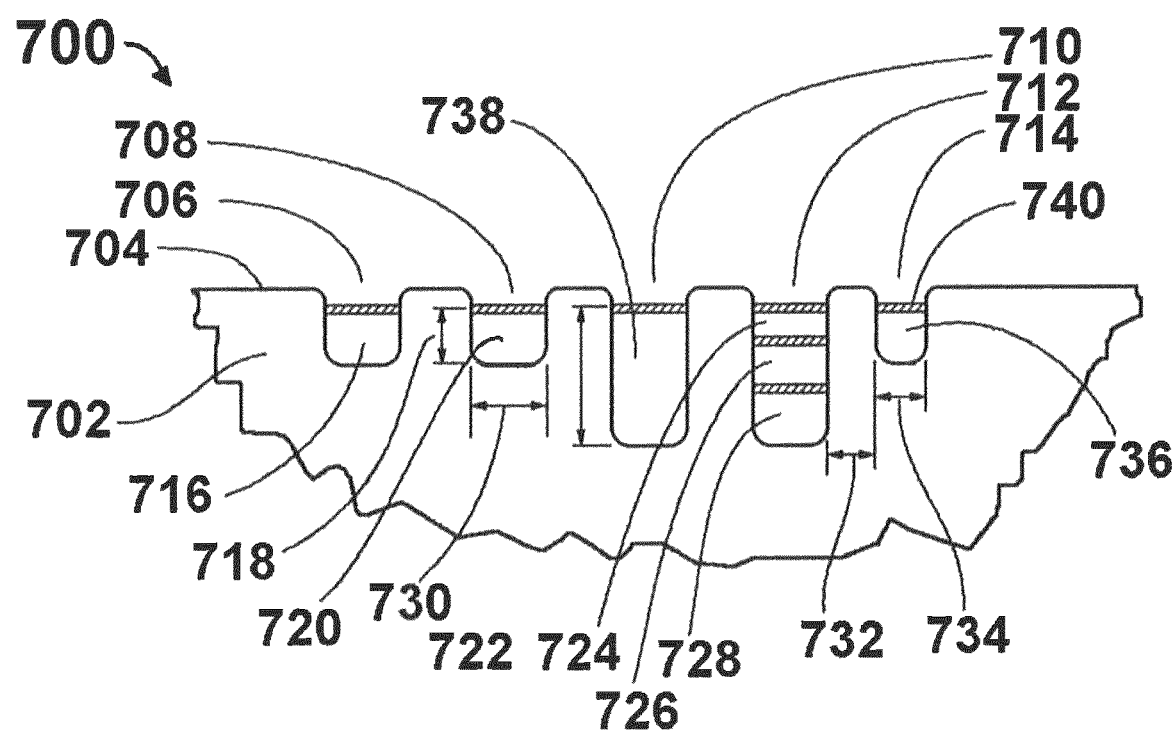
FIG. 5 shows a cross sectional view of the surface of a bone-implantable medical device having a variety of therapeutic agent-loaded holes according to the invention and pointing out the diversity and flexibility of the invention.

FIG. 5 shows a cross sectional view 700 of the surface 704 of a portion 702 of a bone-implantable medical device having a variety of therapeutic agent loaded holes 706, 708, 710, 712, and 714 shown to point out the diversity and flexibility of the invention. The bone-implantable medical device could, for example, be any of a dental implant, a bone screw, an artificial joint prosthesis, or any other bone-implantable medical device. The holes all have thin barrier layers 740 formed according to the invention on one or more layers of therapeutic agent in each hole. For simplicity, not all of the thin barrier layers in FIG. 5 are labeled with reference numerals, but hole 714 is shown containing a first therapeutic agent 736 covered with a thin barrier layer 740 (only thin barrier layer 740 in hole 714 is labeled with a reference numeral, but each cross-hatched region in FIG. 5 indicates a thin barrier layer, and all will hereinafter be referred to by the exemplary reference numeral 740). Hole 706 contains a second therapeutic agent 716 covered with a thin barrier layer 740. Hole 708 contains a third therapeutic agent 720 covered with a thin barrier layer 740. Hole 710 contains a fourth therapeutic agent 738 covered with a thin barrier layer 740. Hole 712 contains fifth, sixth, and seventh therapeutic agents 728, 726, and 724, each respectively covered with a thin barrier layer 740. Each of the respective therapeutic agents 716, 720, 724, 726, 728, 736, and 738 may be selected to be a different therapeutic agent material or may be the same therapeutic agent materials in various combinations of different or same. Each of the thin barrier layers 740 may have the same or different properties for controlling elution or release rate and/or for controlling the rate of inward diffusion of water or other biological fluids according to ion beam processing (preferably GCIB processing) principles discussed herein above. Holes 706 and 708 have the same widths and fill depth 718, and thus hold the same volume of therapeutic agents, but the therapeutic agents 716 and 720 may be different therapeutic agents for different therapeutic modes. The thin barrier layers 740 corresponding respectively to holes 706 and 708 may have either same or differing properties for providing same or different elution, release, or inward diffusion rates for the therapeutic agents contained in holes 706 and 708. Holes 708 and 710 have the same widths, but differing fill depths, 718 and 722 respectively, thus containing differing therapeutic agent loads corresponding to differing doses. The thin barrier layers 740 corresponding respectively to holes 708 and 710 may have either same or differing properties fix providing same or different elution, release, or inward diffusion rates for the therapeutic agents contained in holes 708 and 710. Holes 710 and 712 have the same widths 730, and have the same fill depths 722, thus containing the same total therapeutic agent loads, but hole 710 is filled with a single layer of therapeutic agent 738, while hole 712 is filled with multiple layers of therapeutic agent 724, 726, and 728, which may each be the same or different volumes of therapeutic agent representing the same or different doses and furthermore may each be different therapeutic agent materials for different therapeutic modes. Each of the thin barrier layers 740 for holes 710 and 712 may have the same or different properties for providing same or different elution, release, or inward diffusion rates for the therapeutic agents contained in the holes. Holes 708 and 714 have the same fill depths 718, but have different widths and thus contain different volumes and doses of therapeutic agents 720 and 736. The thin barrier layers 740 corresponding respectively to holes 708 and 714 may have either same or differing properties for providing same or different elution, release, or inward diffusion rates for the therapeutic agents contained in holes 708 and 714. The overall hole (size, shape, and location) pattern on the surface 704 of the implantable medical device and the spacing between holes 732 may additionally be selected to control distribution of therapeutic agent dose across the surface of the implantable medical device. Thus there are many flexible options in the application of the invention for controlling the types and doses and dose distributions and release sequences and release rates of therapeutic agents contained in the bone-implantable medical devices of the invention.

Although the invention has been described with respect to formation of exemplary HA-infused layers, it is recognized that other osteoinductive agents can equally well be employed in forming the infused layers within the scope of the invention. Although the invention has particularly been described in terms of application to titanium (with titanic surface) and zirconia dental implants, it is recognized that the scope of the invention includes bone-implantable medical devices constructed of a wide variety of other materials. Although the invention has been described with respect to various embodiments and applications in the field of bone-implantable medical devices (dental implants, joint prostheses, etc.), it is understood by the inventors that its application is not limited to that field and that the concepts of GCIB infusion of surface coating materials into the surfaces upon which they reside has broader application in fields that will be apparent to those skilled in the art. It should be realized that this invention is also capable of a wide variety of further and other embodiments within the spirit and scope of the invention and the appended claims.

What is claimed is:

1. A method of modifying a surface of bone-implantable medical device comprising the steps of:
   forming a plurality of holes in the surface of the medical device;
   first loading at least one of the plurality of holes with a first therapeutic agent;
   second loading at least another one of the plurality of holes with a second therapeutic agent that is different from the first therapeutic agent;
   first irradiating an exposed surface of the first therapeutic agent in the at least one loaded hole with a first ion beam to firm a first barrier layer at the exposed surface in the at least one loaded hole; and
   second irradiating an exposed surface of the second therapeutic agent in the at least another loaded hole with an ion beam to form a second barrier layer at the exposed surface in the at least another loaded hole,
   wherein the first barrier layer and the second barrier layer have different properties for controlling elution rate of the first and second therapeutic agents.

2. The method of claim 1, wherein the plurality of holes are disposed on the surface in a predetermined pattern to distribute the first and second therapeutic agents on the surface according to a predetermined distribution plan.

3. The method of claim 2, wherein at least one of the plurality of holes is loaded with a first quantity of the first therapeutic agent that differs from a second quantity of the first therapeutic agent loaded in at least another of the plurality of holes.

4. A method of modifying a surface of bone-implantable medical device comprising the steps of:
   forming one or more holes in the surface of the medical device;
   first loading at least one hole of the one or more holes with a first therapeutic agent without completely filling the at least one hole;
   first irradiating an exposed surface of the therapeutic agent in the at least one incompletely filled hole with a first ion beam to form a first barrier layer at the exposed surface of the first therapeutic agent;
   following the first irradiating step, second loading the at least one incompletely filled hole with a second therapeutic agent overlying the first barrier layer; and
   second irradiating an exposed surface of the second therapeutic agent in the at least one incompletely filled hole with a second ion beam to form a second barrier layer at the exposed surface of the second therapeutic agent,
   wherein the first barrier layer and the second barrier layer have different properties for controlling elution rate of the first and second therapeutic agents.

5. The method of claim 1, wherein the first ion beam is a first gas cluster ion beam and further wherein the second ion beam is a second gas cluster ion beam.

6. The method of claim 4, wherein the first ion beam is a first gas cluster ion beam and further wherein the second ion beam is a second gas cluster ion beam.

* * * * *

UNITED STATES PATENT AND TRADEMARK OFFICE
CERTIFICATE OF CORRECTION

| | | |
|---|---|---|
| PATENT NO. | : 9,005,696 B2 | Page 1 of 1 |
| APPLICATION NO. | : 13/746456 | |
| DATED | : April 14, 2015 | |
| INVENTOR(S) | : Richard C. Svrluga et al. | |

It is certified that error appears in the above-identified patent and that said Letters Patent is hereby corrected as shown below:

In the Claims

Col. 12, line 21, Claim 1, line 12, second word from the left: the word [[firm]] should be corrected to -- form --

Signed and Sealed this
Twenty-first Day of July, 2015

Michelle K. Lee
*Director of the United States Patent and Trademark Office*